(12) United States Patent
DeToro et al.

(10) Patent No.: US 7,112,181 B1
(45) Date of Patent: Sep. 26, 2006

(54) TRI-PLANAR ORTHOSIS

(75) Inventors: William DeToro, Poland, OH (US); Brian Perala, Geneva, OH (US); Michael Banks, Lakewood, OH (US)

(73) Assignee: Anatomical Concepts, Inc., Boardman, OH (US)

( * ) Notice: Subject to any disclaimer, the term of this patent is extended or adjusted under 35 U.S.C. 154(b) by 561 days.

(21) Appl. No.: 10/407,662

(22) Filed: Apr. 7, 2003

(51) Int. Cl.
*A61F 5/00* (2006.01)

(52) U.S. Cl. .......................................... 602/27

(58) Field of Classification Search ............ 602/27–29, 602/23, 5, 1, 16, 65; 128/846, 869, 882, 128/892
See application file for complete search history.

(56) References Cited

U.S. PATENT DOCUMENTS

| | | | |
|---|---|---|---|
| 2,482,646 A * | 9/1949 | Brachman et al. ............ | 602/29 |
| 2,630,801 A * | 3/1953 | Mest et al. .................... | 602/24 |
| 2,967,360 A * | 1/1961 | Rice ............................. | 36/140 |
| 3,171,407 A * | 3/1965 | Rogers ......................... | 602/24 |
| 3,892,231 A * | 7/1975 | Tummillo .................... | 602/24 |
| 5,088,479 A | 2/1992 | DeToro | |
| 5,267,949 A * | 12/1993 | De La Torre et al. ........ | 602/24 |
| 5,431,624 A * | 7/1995 | Saxton et al. ................. | 602/27 |
| 5,486,157 A * | 1/1996 | DiBenedetto ................ | 602/27 |
| 5,545,127 A * | 8/1996 | DeToro ....................... | 602/27 |
| 5,593,383 A | 1/1997 | DeToro | |
| 5,908,398 A | 6/1999 | DeToro | |
| 5,944,679 A | 8/1999 | DeToro | |
| 5,961,477 A * | 10/1999 | Turtzo .......................... | 602/27 |
| 6,036,665 A * | 3/2000 | Towsley ....................... | 602/23 |
| 6,056,712 A * | 5/2000 | Grim ............................ | 602/27 |
| 6,302,858 B1 * | 10/2001 | DeToro et al. ................. | 602/5 |

* cited by examiner

*Primary Examiner*—Michael A. Brown
*Assistant Examiner*—Auong Q. Pham
(74) *Attorney, Agent, or Firm*—Harpman & Harpman

(57) ABSTRACT

An ankle and foot orthosis brace for use in supporting, immobilizing and correction of physical anomalies associated with a patient's ankle or foot. The brace is of a multi-part construction having a generally L-shaped configuration with a contoured upper leg support and a foot support portion interconnected by a multi-planar adjustment hinge and bi-lateral bearing assemblies there between. A foot pad with apertured tabs extending there from being part of the foot portion with adjustable fabric fasteners extending from the foot portion and the leg portion securing the brace to the patient's leg and foot.

10 Claims, 7 Drawing Sheets

TRI-PLANAR ORTHOSIS

BACKGROUND OF THE INVENTION

1. Technical Field

This invention relates to therapeutic leg and foot braces, more particularly to a securing apparatus therefore having a foot pad, a fabric foot engagement enclosure for releaseably securing the brace to the foot and ankle of the patient to provide and maintain a constant pressure against the foot, sole and ankle of the patient for therapeutic purposes including adducted and abducted conditions of the foot.

2. Description of Prior Art

An orthotic foot and ankle brace typically has an L-shaped construction with a contoured leg support portion, a foot portion, and an interconnecting heel portion connected there between. An integral fabric foot engagement enclosure is provided to secure the brace to the patient's foot and ankle.

Prior art devices of this type provide for a variety of leg, ankle and foot stabilization utilizing two-part brace assemblies interconnected by free hinges of elastomeric material as seen in U.S. Pat. No. 5,496,263 that permit the tolocural articulation to move about a single axis.

Other prior art patents such as U.S. Pat. No. 5,431,624 discloses leg and foot braces having adjustable angles between the two sections with an extended ground engagement sole and a cam action locking assembly.

U.S. Pat. No. 5,486,157 discloses a hinge at the apex of a contoured heel portion to provide free dorsiflextion and plantar-flexion with a pivot point below the hinges for inversion, eversion and pronation and supination of the foot.

Applicant's own U.S. Pat. Nos. 5,088,479, 5,545,127, 5,593,383, 5,908,398, 5,944,679 and 6,302,858 B1 define the present state of the art in ankle and foot orthosis beginning with resilient L-shaped construction in U.S. Pat. No. 5,088,479, the introduction of lateral adjustable ankle and foot orthosis in U.S. Pat. No. 5,545,127, adjustable ankle and foot orthosis brace having adjustable hinge assembly between the leg configuration and heel configuration, in U.S. Pat. No. 5,908,398 a compound adjustable ankle and foot orthosis brace, in U.S. Pat. No. 6,302,858 B1 having a unique intermedial transition portion with adjustable multi-angular bearing surfaces to impart selective angular inclination both laterally and dorsi/plantar flexion by respective multiple overlapping intermedial end portions of respective resilient interconnecting portions.

Additional prior art devices can be seen in U.S. Pat. Nos. 5,961,477 and 6,056,712.

In 5,961,477 an ankle and foot orthosis can be seen having a one piece L-shaped support member interconnected to a foot portion having a walking sole thereon.

In U.S. Pat. No. 6,056,712 a multi-functional orthosis for the foot, heel, ankle and lower leg is disclosed in which an upper leg engagement portion has adjustable locking hinge assembly on either side of the dorsi and plantar flexion positioning.

SUMMARY OF THE INVENTION

An ankle and foot orthosis device for supporting and selectively immobilizing a patient's ankle and foot having a tri-planer adjustment in frontal, sagittal and transverse planes. The orthotic brace comprises a leg portion, a foot portion with an interconnecting heel portion having multi-angular adjustment bearing surfaces for dorsi-plantar flexion, bi-lateral adjustment and trans-axial rotation of the leg and heel portion with respect to the foot portion. Multiple overlapping intermedial end portions at the distal end of the respective resilient interconnecting heel portions allow for tri-planer adjustment.

OBJECTS AND ADVANTAGES

It is the object of the present invention to provide an incremental adjustable limit of bi-lateral angular inclination and imputable limited degrees of plantar flexion and dorsi-flexion in the sagittal plane as well as axial rotation adjustment in the transverse plane to address the specific problems of adducted condition in which the foot turns inwardly towards the mid-line of the body and abducted foot condition in which the foot turns outwardly from the mid-line of the body that can be addressed and corrected by adjustment of the transverse axial plane of the foot portion in relation to the leg portion.

DESCRIPTION OF THE PREFERRED EMBODIMENT

Figure 1:
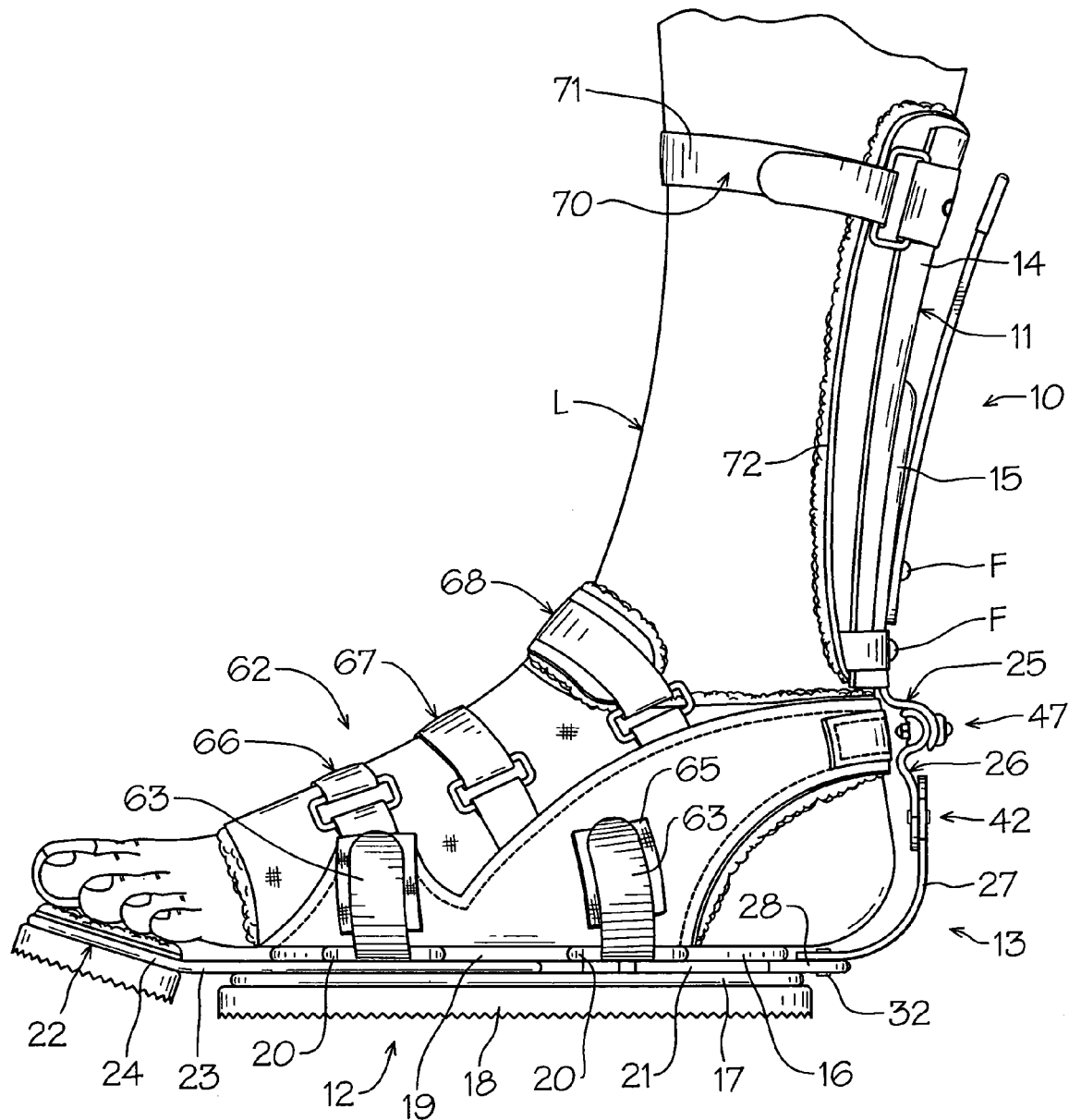
FIG. 1 is a side elevational view of the present invention.
Figure 2:
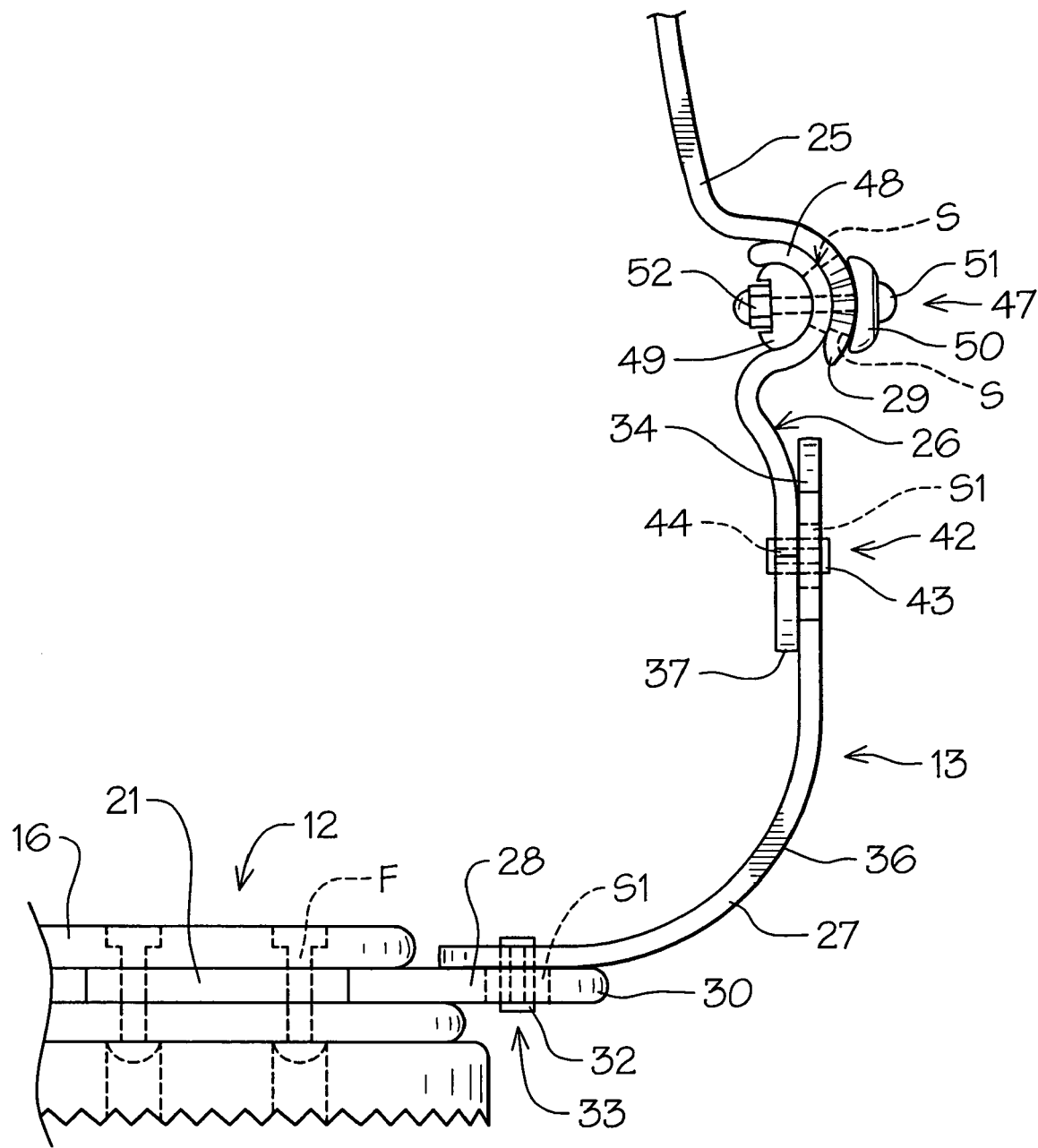
FIG. 2 is an enlarged partial side elevational view thereof.

Referring now to FIGS. 1 and 2 of the drawings, a tri-planer ankle and foot orthosis brace 10 of the invention can be seen having a leg portion 11, a foot portion 12 and an interconnecting multi-part heel portion 13 extending there between. The leg portion 11 has an elongated transversely contoured leg support 14 having a recessed channel 15 formed inwardly from one end thereof. The foot portion 12 has a foot pad 16 connected to a generally rectangular attachment brace 17. The attachment brace 17 has a resilient walking pad 18 secured thereto. The foot pad 16 is of a generally rectangular configuration with an area of reduced transverse dimension at 19 which defines pairs of longitudinally spaced oppositely disposed aperture tabs 20 thereon.

A mounting bracket 21 extends downwardly from the bottom of the foot pad 16 adjacent one end thereof for registering engagement with the heel portion 13 between the foot pad 16 and abutting attachment base 17.

In practice, the leg and foot portions are made of synthetic plastic resin material so they can be molded or pre-formed to the desired contour required for engagement with a patient's leg L shown in broken lines in FIG. 1 of the drawings.

A toe extension member 22, best seen in FIG. 1 of the drawings, is adjustably secured to the foot pad 16 opposite the mounting bracket 21 hereinbefore described. The toe extension member 22 has a flat base area 23 with an upturned angularly offset end portion 24. The toe extension member 22 is registerably attached between the foot pad 16 and the attachment brace 17 by fasteners F (not shown) extending from the foot pad 16 so as to allow for longitudinal adjustment thereto. The interconnecting heel portion 13 comprises an upper leg element 25, a first intermediate bearing engagement element 26, a second intermediate bearing engagement element 27 and a lower foot engagement element 28, all of which are comprised of a metal alloy or other suitable material.

The upper leg element 25 is secured within the recess channel 15 of the leg support 14 by fasteners F and has an articulated curved free end at 29, best seen in FIG. 2 of the drawings.

The foot engagement element 28 extends from and is secured within the hereinbefore described mounting bracket 21 of the foot pad 16 by a pair of fasteners F, shown in dotted lines, that inter-engage there through in registration with selective fixed apertures in the mounting bracket 21. The foot engagement element 28 has an apertured free end at 30 with a pair of transversely spaced articulated slots S1 within and a pivot opening at PO-1 there between, best seen in FIG. 4 of the drawings.

Figure 3:
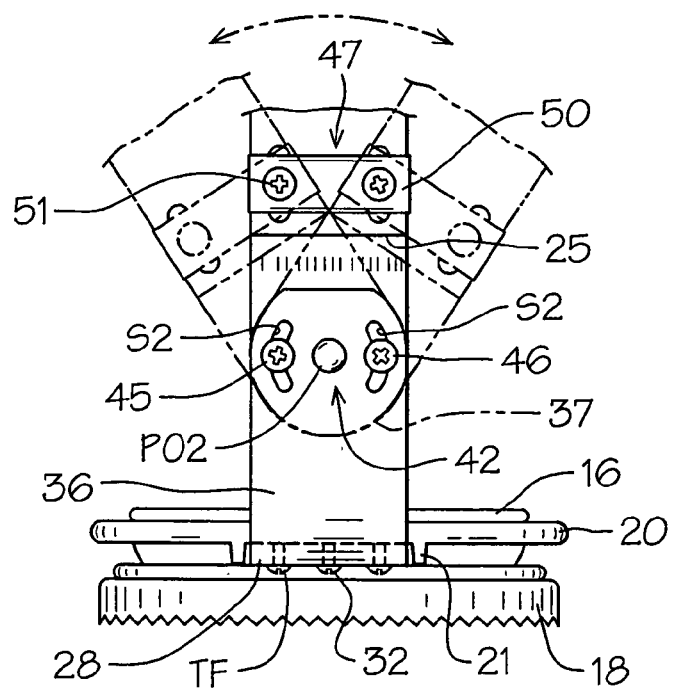
FIG. 3 is a partial rear elevational view thereof with portions broken away.
Figure 4:
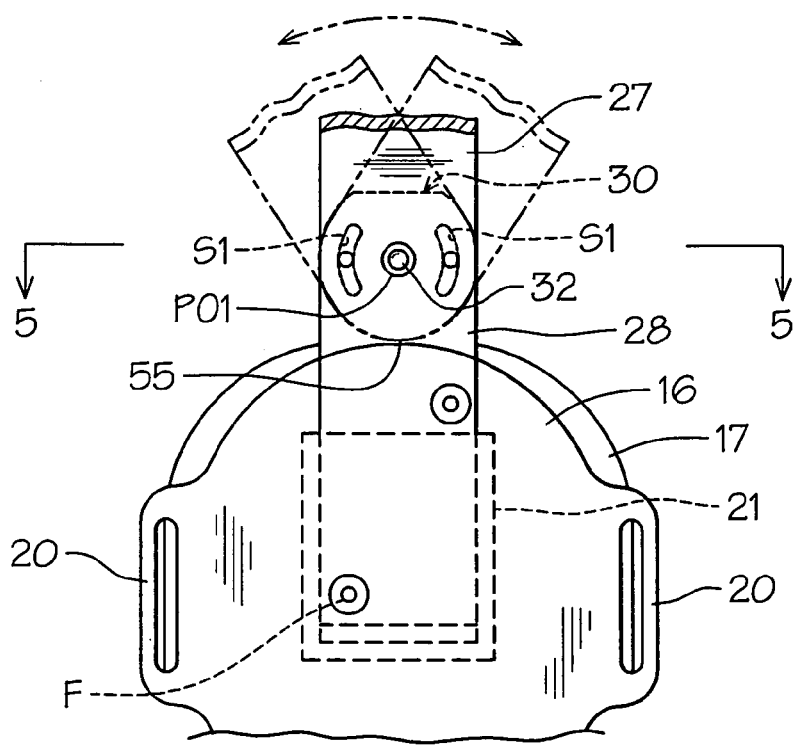
FIG. 4 is a partial top plan view thereof with portions broken away.

The second intermediate bearing engagement element 27 is adjustably secured to the apertured free end 30 of the foot engagement element 28 by a central pivot pin 32 and a pair of threaded stop limit fasteners TF extending through the slots S1 and threadably disposed into said first intermediate bearing engagement element 27, best illustrated in FIGS. 2, 3 and 4 of the drawings defining a trans-axial pivot fitting assembly 33.

The bearing engagement element 27 is curved at 36 with an upper articulated arcuate end 31 having a pair of transversely spaced arcuate slots S2 therein and a pivot opening PO2 there between as best illustrated in FIG. 3 of the drawings.

Accordingly, an overlapping apertured curved free end 37 of the intermediate bearing engagement element 26 and the apertured pivot engagement end 31 of the intermediate bearing engagement element 27 define a trans-lateral pivot fitting assembly 42. A pivot pin 43 interconnects said respective overlapping ends 37 and 31 extending through the pivot opening PO2 and aligned apertures at 44 in the first intermediate bearing element 26 respectively and aligned apertures therein.

A pair of oppositely disposed stop limit threaded fasteners 45 and 46 are threadably secured into registering threaded apertures in the pivot engagement end 37 of the intermediate bearing engagement element 26 through the respective aligned slots S2 in the overlapping free end portion 31 of the intermediate bearing engagement element 27 as hereinbefore described.

A hinge assembly 47 is formed by the overlapping articulated free end 29 and a curved slotted free end portion 48 of the first intermediate bearing engagement element 26 having a hinge block 49 registerable therein and correspondingly a compression cap fitting 50 with a curved inter-engagement surface 51 positioned over the aligned slots S in the articulated curved free end 29 of the leg element 25 and oppositely disposed aligned relation to the hinge block 49. The hinge block 49 and compression cap fitting 50 are registerably secured together by a pair of threaded fasteners 51 extending through aligned apertures therein and the corresponding aligned slots S of the respective upper leg element 25 and first intermediate bearing engagement element 26 and threadably engaged by lock nuts 52, best illustrated in FIG. 2 of the drawings.

In use, three distinct planar angular adjustments can be made independently or in a variety of combinations to achieve the desired therapeutic effect as thus illustrated.

The second pivot fitting assembly 42 allows for the intermediate bearing engagement element 26 and associated leg portion 11 to be disposed laterally in relation to the intermediate bearing engagement element 27 and the foot portion 12 when the pivot fitting assembly 33 is in centrally aligned locked position as will be discussed in greater detail hereinafter.

The lateral adjustment of the second pivot fitting assembly 42 is indicated in broken lines in FIG. 3 of the drawings with incremental adjustability achieved by alignment of indicator groove 53 on the pivot end 34 of the intermediate bearing engagement element 27 as illustrated with multiple incrementally radially spaced indicator grooves 54 formed inwardly of the free end 37 of the intermediate bearing element 26. Once the desired degree of lateral alignment is achieved, the stop limit fasteners 45 and 46 are secured locking to so aligned overlapping pivot engagement ends 34 and 37 respectively together.

Figure 5:
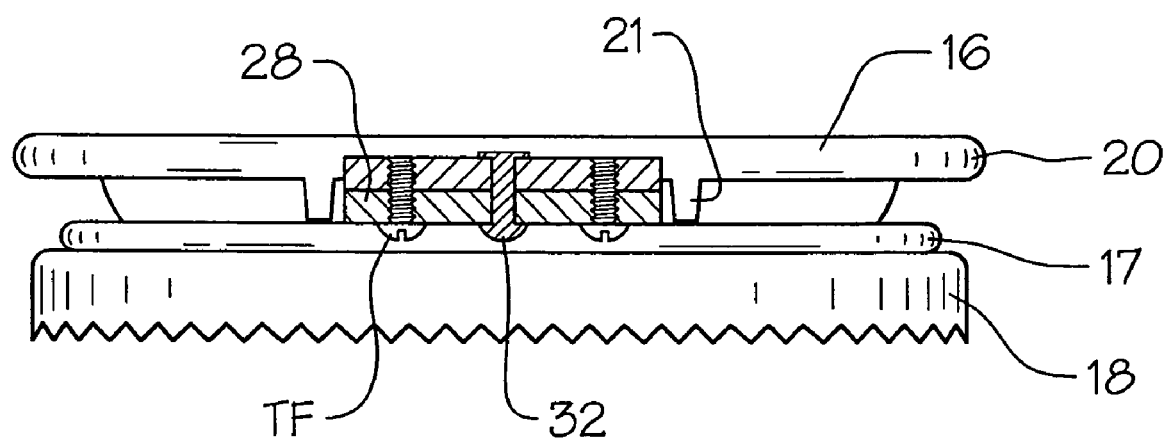
FIG. 5 is an enlarged cross-section on lines 5—5 of FIG. 4.
Figure 6:
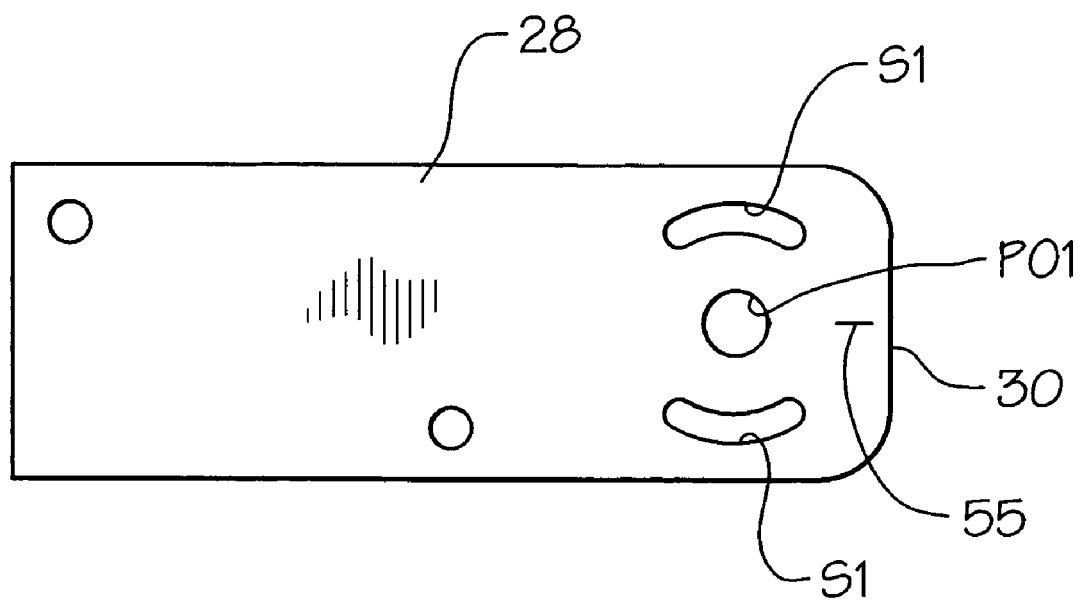
FIG. 6 is an enlarged top plan view of a portion of the foot engagement element portion shown in FIG. 2.
Figure 7:
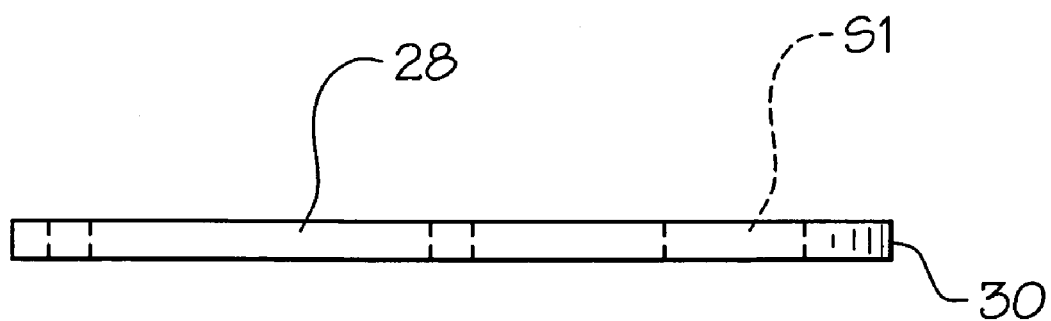
FIG. 7 is an enlarged side elevational view thereof.
Figure 8:
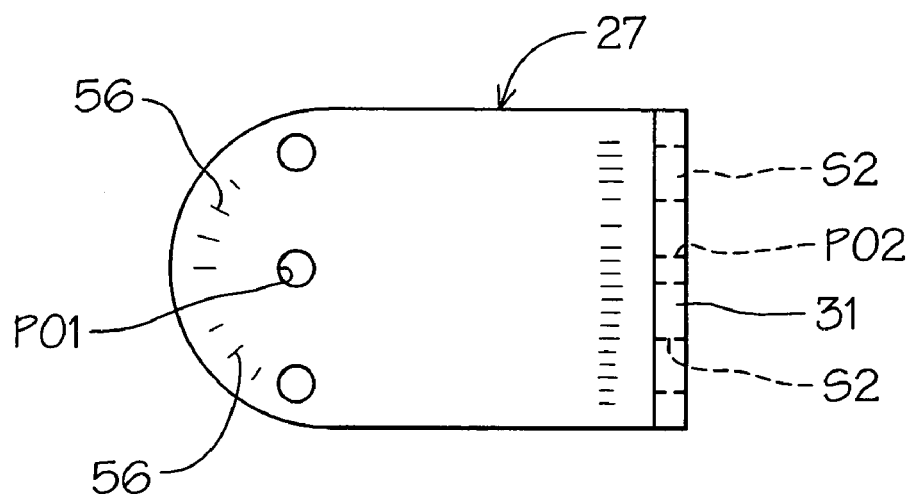
FIG. 8 is an enlarged top plan view of a second intermedial portion shown in FIG. 2.
Figure 9:
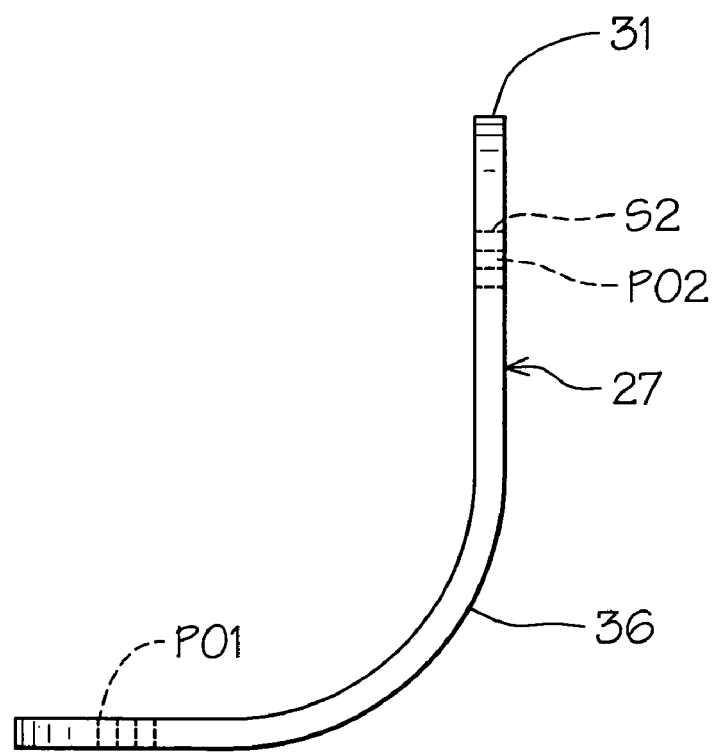
FIG. 9 is an enlarged side elevational view thereof.

Referring now to FIGS. 1, 4 and 5 of the drawings, the trans-axial pivot fitting assembly 33 of the invention will provide for trans-axial lateral adjustment indicated in broken lines in FIG. 4 of the drawings between the foot engagement element 28 and the second intermediate bearing engagement element 27. Incremental adjustment is achieved by loosening of the set bolt fasteners TF and aligning a trans-axial indicator groove 55 in the foot engagement element 28 with multiple radially spaced indicator grooves 56 in the surface of the intermediate bearing engagement element 27 adjacent its respective free ends shown in broken lines in FIG. 4 of the drawings. This trans-axial lateral adjustment allows for the unique axial rotation of the leg portion 11 and heel portion 13 with respect to the foot portion 12 to address the clinical treatment of abduction and adduction of the patient's foot by applying incrementally adjustable pressure thereon to correct in stages the hereinbefore described clinical conditions.

Figure 10:
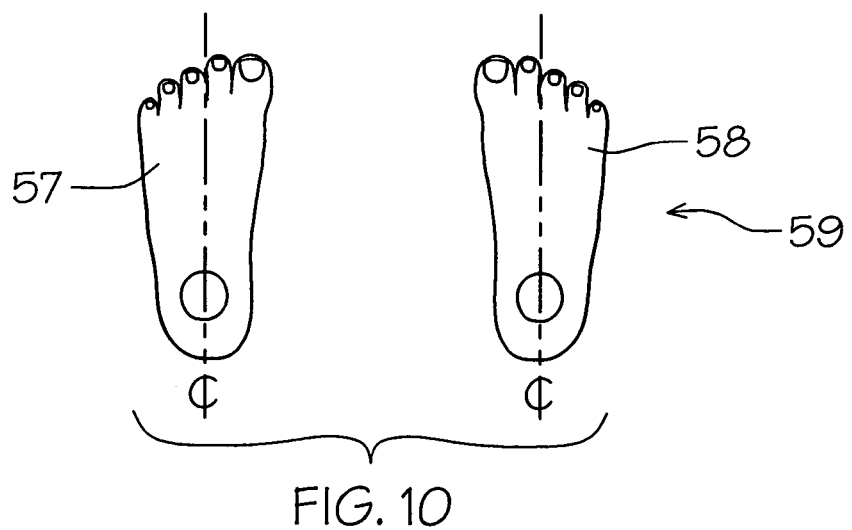
FIG. 10 is a graphic top plan representation of normal foot position of a patient.
Figure 11:
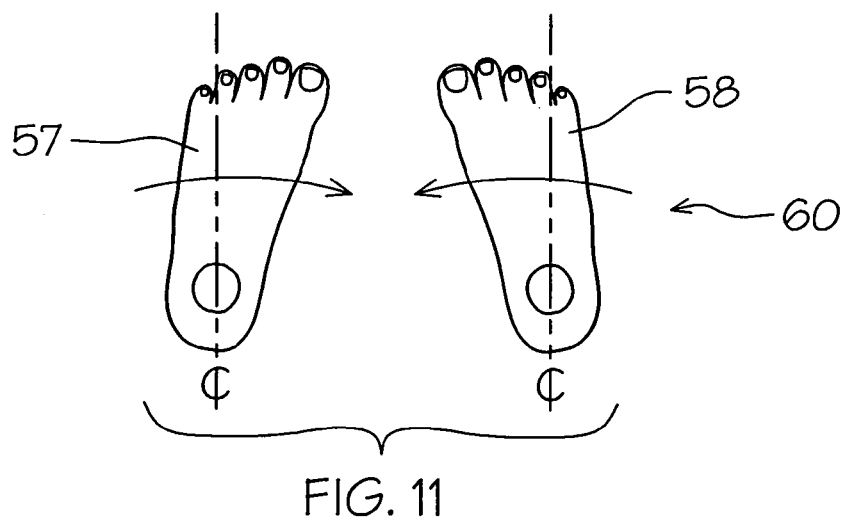
FIG. 11 is a graphic top plan representation of an adducted foot condition of a patient.
Figure 12:
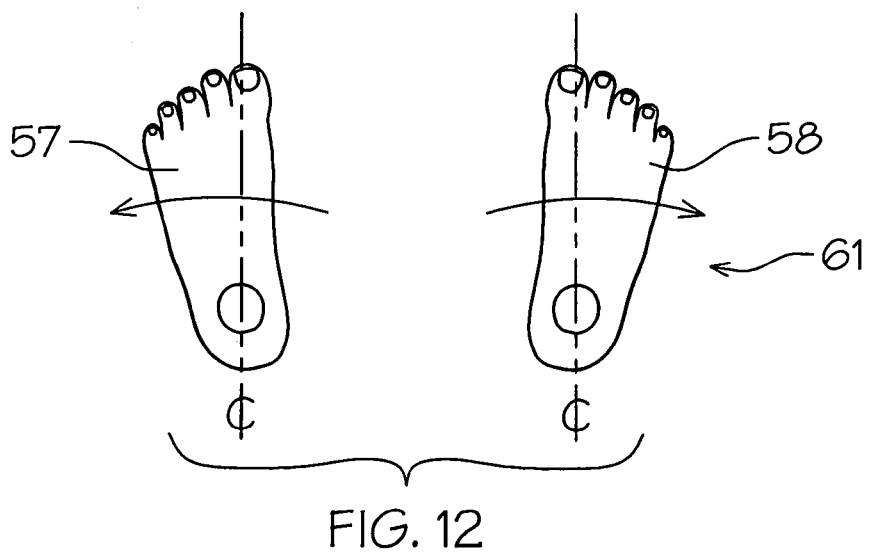
FIG. 12 is a graphic top plan representation of an abducted foot condition of a patient.

Referring now to FIGS. 10, 11 and 12 of the drawings, graphic illustrations of human feet 57 and 58 are shown depicting normal foot orientation at 59 in FIG. 10 of the drawings and adducted condition at 60 in FIG. 11 of the drawings in which the feet 57 and 58 are turned inwardly towards one another. In FIG. 12 of the drawings, an abducted condition 61 is illustrated in which feet 57 and 58 are turned outwardly from one another.

It will be seen by applying an incremental angular rotational displacement of the respective feet 57 and 58 by the main adjustable pivot fitting assembly 33 of the tri-planar orthotic brace 10 of the invention can correct these conditions.

In use, the brace 10 can be readily adjusted in multiple planes to accommodate the patient's foot and associated conditions. Then, as noted, by incremental adjustment of the main pivot fitting assembly 33 will provide positive resistance to the foot curvature alignment over a prolonged period of time, the pressure on the foot and its tissue diminish thus altering the effects of the abduction of adduction as set forth hereinbefore.

Referring back to FIG. 1 of the drawings, the foot portion 12 is illustrated comprising a fabric foot engagement enclosure 62 that is removably secured to the foot pad 16 by a plurality of attachment strips 63 that extend from the foot engagement enclosure 62 through the aperture tabs 20 and back against themselves onto interlocking hook and loop fastening material inserts 65 thereon as will be well understood by those skilled in the art.

Secondary enclosure straps and buckle assemblies 66, 67 and 68 provide for overlapping closure of the foot engagement enclosure 62.

A leg attachment strap assembly 70 is secured to and extend from the leg portion 11 adjacent is respective upper and lower free ends.

A leg attachment strap 71 secures the patient's upper leg L shown in broken lines to a fabric pad 72 secured independently to the leg portion 11 by the use of hook and loop fastener materials as hereinbefore described.

It will be apparent from the above description that the present invention provides for stable accommodations of a patient's particular range of dorsiflexion and plantarflexion motion with the incremental adjustment degree of lateral angular inclination as well as the axial trans-lateral rotational adjustment by use of the hereinbefore described composite hinge, bi-lateral pivot assembly and trans-lateral axial rotation pivot tri-planar assembly.

It will thus be seen and apparent to those skilled in the art that various changes and modifications may be made therein to the invention.

The invention claimed is:

1. A tri-planar adjustable therapeutic leg and foot brace for use on a patient comprising in combination, a foot portion pivotally connected to a substantially rigid leg portion having an upper engageable leg support extending there from, an upper leg element extends from said upper engageable leg support, a first and second intermediate bearing engagement elements and a foot engagement element, the free end of said upper leg element is adjustably engaged with an end of said first intermediate bearing element, wherein said engaged ends have C-shaped overlapping end portions with an adjustable apertured locking hinge assembly thereon, said first and second intermediate bearing engagement elements have respective overlapping free end portions movable pivotally and laterally with respect to one another, said foot engagement element and said second intermediate bearing engagement element having overlapping free ends movable pivotally and laterally on a horizontal plane in respect to one another by to impart axial rotation to said upper leg element in relation to said foot portion, said foot engagement element includes a pair of transversely spaced and oppositely disposed arcuated slots disposed on the free end of the foot engagement element, a pivot opening; wherein a pair of stop limit means extend through said pair of arcuated slots to provide lateral adjustment and axial rotation of said second intermediate bearing engagement element relative to said foot engagement element.

2. The tri-planar adjustable therapeutic leg and foot brace set forth in claim 1 wherein said apertured locking hinge assembly comprises, an apertured hinge block and an apertured compression cap, the apertured compression cap being in aligned relationship with said apertured hinge block, fasteners extending through the apertures of said hinge block and compression cap and through an opening in each of said C-shaped overlapping end portions.

3. The tri-planar adjustable therapeutic leg and foot brace set forth in claim 1 further comprises, a pivot pin extending through said pivot opening.

4. The tri-planar adjustable therapeutic leg and foot brace set forth in claim 1 wherein said foot portion further comprises an attachment brace, a resilient walking pad secured to said attachment brace and an adjustable toe extension member extensively positioned in relation thereto.

5. The tri-planar adjustable therapeutic leg and foot brace set forth in claim 1 wherein said foot engagement element secured to said foot portion is preferably made of resilient metal material.

6. The tri-planar adjustable therapeutic leg and foot brace set forth in claim 1 wherein said first and second intermedial bearing engagement element are preferably made of resilient metal material.

7. The tri-planar adjustable therapeutic leg and foot brace set forth in claim 1 wherein said pair of stop limit means comprising threaded fasteners.

8. A tri-planar adjustable therapeutic leg and foot orthosis brace for use on a patient comprising; a foot portion, a leg portion, an upper leg element extend from said leg portion, first and second intermediate bearing engagement elements pivotally connected to each other, and a foot engagement element pivotally secured to the second intermediate bearing engagement element, an adjustable hinge assembly interconnecting said upper leg element and said first intermediate bearing engagement element, a first means pivotally interconnecting overlapping free end portions of said second intermediate bearing engagement element and said first intermediate bearing engagement element, a second means pivotally interconnecting overlapping free end portions of said foot engagement element and said second intermediate bearing engagement element, said foot engagement element and said second intermediate bearing engagement element movable pivotally and trans-laterally on a horizontal plane in respect to one another, said second pivotally interconnecting means comprising, a pivot pin, a pair of transversely spaced and oppositely disposed arcuated slots disposed on the free end portion of the foot engagement element, and a pair of stop limit means registerably engaged within said arcuated slots therein to provide lateral adjustment and axial rotation of said second intermediate bearing engagement element relative to said foot engagement element.

9. The tri-planar adjustable therapeutic leg and foot brace set forth in claim 8 wherein said foot portion further comprises an attachment brace, a resilient walking pad secured to said attachment brace and an adjustable toe extension member extensively positioned in relation thereto.

10. The tri-planar adjustable therapeutic leg and foot orthosis brace set forth in claim 8 wherein said first and second intermediate bearing engagement elements and said upper leg element extending from said leg portion and said foot engagement pivot bearing element extending from said foot portion are preferably made of resilient metal material.

* * * * *